(12) United States Patent
McMahon et al.

(10) Patent No.: US 11,065,029 B2
(45) Date of Patent: Jul. 20, 2021

(54) EXPANDABLE BALLOON

(71) Applicant: VERYAN MEDICAL LIMITED, Oxford (GB)

(72) Inventors: Tony McMahon, Quin (IE); Martin G. Burke, Horsham (GB); Kevin B. Heraty, Castlebar (IE); Nicholas Yeo, Horsham (GB)

(73) Assignee: VERYAN MEDICAL LIMITED, Oxford (GB)

( * ) Notice: Subject to any disclaimer, the term of this patent is extended or adjusted under 35 U.S.C. 154(b) by 0 days.

(21) Appl. No.: 14/787,381

(22) PCT Filed: May 2, 2014

(86) PCT No.: PCT/GB2014/051385
§ 371 (c)(1),
(2) Date: Oct. 27, 2015

(87) PCT Pub. No.: WO2014/177893
PCT Pub. Date: Nov. 6, 2014

(65) Prior Publication Data
US 2016/0095619 A1    Apr. 7, 2016

Related U.S. Application Data

(60) Provisional application No. 61/818,592, filed on May 2, 2013.

(51) Int. Cl.
*A61B 17/3207*   (2006.01)
*A61M 25/10*     (2013.01)
*A61B 17/22*     (2006.01)

(52) U.S. Cl.
CPC .. *A61B 17/320758* (2013.01); *A61B 17/3207* (2013.01); *A61B 17/320725* (2013.01);
(Continued)

(58) Field of Classification Search
CPC ............ A61M 25/1002; A61M 25/104; A61M 25/10; A61M 25/1011; A61M 2025/1086;
(Continued)

(56) References Cited

U.S. PATENT DOCUMENTS 5,295,959 A * 3/1994 Gurbel ............... A61M 25/104
                                                    604/103
5,649,978 A   7/1997 Samson
(Continued)

FOREIGN PATENT DOCUMENTS

GB    2 430 373 A    3/2007
JP    2007-502694 A  2/2007
(Continued)

OTHER PUBLICATIONS

International Search Report of International Application No. PCT/GB2014/051385 dated Oct. 14, 2014, 8 pages.
(Continued)

*Primary Examiner* — Mohamed G Gabr
(74) *Attorney, Agent, or Firm* — Fay Sharpe LLP

(57) ABSTRACT

An expandable balloon, for insertion in a vessel of the human or animal body, is movable between a collapsed condition and an expanded condition. The balloon includes a plaque disrupting formation arranged to be on an outer surface of the balloon when in the expanded condition. When in the expanded condition, the balloon has a centre line which follows a substantially helical path.

20 Claims, 5 Drawing Sheets

(52) U.S. Cl.
CPC .............. *A61M 25/1002* (2013.01); *A61B 2017/22061* (2013.01); *A61B 2017/320733* (2013.01); *A61M 25/104* (2013.01); *A61M 2025/1086* (2013.01)

(58) Field of Classification Search
CPC .... A61M 2025/006; A61M 2025/1004; A61M 2025/1084; A61M 2025/1097; A61F 2230/0091; A61F 2250/0098; A61F 2250/0067; A61F 2002/068; A61F 2002/3008; A61F 2002/32089; A61F 2210/076; A61B 17/320758; A61B 17/3207; A61B 17/320725; A61B 17/22032; A61B 2017/2206; A61B 2017/22061; A61B 2017/22034; A61B 2017/320733
USPC .......................................................... 606/159
See application file for complete search history.

(56) References Cited

U.S. PATENT DOCUMENTS

| | | | |
|---|---|---|---|
| 5,997,516 A | 12/1999 | Caro et al. | |
| 6,039,754 A | 3/2000 | Caro | |
| 6,129,706 A * | 10/2000 | Janacek | A61M 25/1002 604/103.08 |
| 6,450,988 B1 * | 9/2002 | Bradshaw | A61N 5/1002 600/3 |
| 6,554,856 B1 | 4/2003 | Doorly et al. | |
| 7,326,240 B1 | 2/2008 | Caro et al. | |
| 8,226,704 B2 | 7/2012 | Caro et al. | |
| 8,236,043 B2 | 8/2012 | Caro et al. | |
| 9,149,377 B2 | 10/2015 | Heraty et al. | |
| 9,539,120 B2 | 1/2017 | Heraty et al. | |
| 9,597,214 B2 | 3/2017 | Heraty et al. | |
| 9,907,679 B2 | 3/2018 | Caro et al. | |
| 10,456,276 B2 | 10/2019 | Taylor et al. | |
| 2002/0151918 A1 | 10/2002 | Lafontaine et al. | |
| 2003/0114920 A1 | 6/2003 | Caro et al. | |
| 2004/0143287 A1 * | 7/2004 | Konstantino | A61B 17/320725 606/194 |
| 2007/0021707 A1 | 1/2007 | Caro et al. | |
| 2007/0156078 A1 | 7/2007 | Caro et al. | |
| 2009/0293574 A1 | 12/2009 | Caro | |
| 2010/0094403 A1 * | 4/2010 | Heraty | A61F 2/958 623/1.15 |
| 2010/0121372 A1 * | 5/2010 | Farnan | A61F 2/86 606/194 |
| 2010/0286759 A1 * | 11/2010 | Taylor | A61F 2/94 623/1.15 |
| 2011/0152683 A1 * | 6/2011 | Gerrans | A61B 17/22012 600/435 |
| 2012/0059401 A1 * | 3/2012 | Konstantino | A61F 2/958 606/159 |
| 2012/0245520 A1 | 9/2012 | Kelly et al. | |
| 2013/0204179 A1 * | 8/2013 | Konstantino | A61B 17/320725 604/22 |
| 2014/0088624 A1 * | 3/2014 | Burton | A61M 25/1002 606/159 |
| 2014/0277002 A1 * | 9/2014 | Grace | A61B 17/22 606/159 |

FOREIGN PATENT DOCUMENTS

| | | |
|---|---|---|
| JP | 2007-521878 A | 8/2007 |
| JP | 2008-506454 A | 3/2008 |
| JP | 2008-526312 A | 7/2008 |
| JP | 2016-521169 A | 7/2016 |
| WO | WO 2004/066852 A2 | 8/2004 |
| WO | WO 2005/076833 A2 | 8/2005 |
| WO | WO 2006/016938 A1 | 2/2006 |
| WO | WO 2006/073933 A2 | 7/2006 |
| WO | WO 2008/125842 A1 | 10/2008 |
| WO | WO 2009/002855 A2 | 12/2008 |

OTHER PUBLICATIONS

Written Opinion of International Application No. PCT/GB2014/051385 dated Oct. 14, 2014, 9 pages.

* cited by examiner

EXPANDABLE BALLOON

BACKGROUND

This invention relates to an expandable balloon for insertion in a fluid conduit of the human or animal body.

Atherosclerosis affects the blood vessels of patients with coronary arterial disease or with peripheral arterial disease. Peripheral arterial disease may affect the carotid or the arteries of the lower limbs. For example, peripheral arterial disease in the femoropopliteal artery often takes the form of total occlusions or calcified, obstructive lesions. Percutaneous transluminal angioplasty (PTA) is often the initial treatment choice to restore lumen patency or to prepare a vessel, moderately or severely affected by atherosclerotic disease, for stenting. One of the major problems with PTA in such settings is an uncontrolled disruption of the atherosclerotic plaque leading to vessel dissection.

An alternative method to treat such lesions is to use a cutting/scoring balloon. The principle behind the cutting/scoring balloon is to apply a longitudinal focal force to the atherosclerotic plaque, which is understood to reduce the uncontrolled disruption of the atherosclerotic plaque associated with traditional PTA techniques. By using a cutting/scoring balloon the plaque may be disrupted in a controlled manner, helping to achieve the process of dilatation of the stenosis without the risk of damaging the vessel during the application of regular balloon angioplasty. In some cases it is found to be beneficial to provide for distal capture of displaced plaque fragments to avoid downstream embolization.

BRIEF SUMMARY

Viewed from a first aspect the invention provides an expandable balloon for insertion in a vessel of the human or animal body, the balloon being movable between a collapsed condition and an expanded condition, the balloon comprising a plaque disrupting formation arranged to be on an outer surface of the balloon when in the expanded condition, and the balloon having, when in the expanded condition, a centre line which follows a substantially helical path.

A balloon with a helical centreline may tend to exert on a vessel wall higher stresses on the outer curvature of the helix. The plaque disrupting formation can be arranged on the balloon outer surface taking account of this effect.

The plaque disrupting formation may be a cutting or scoring blade, or it may be a wire. The wire may have various cross-sectional shapes, such as square or triangular. The blade or wire may be formed from a shape memory material, such as nitinol, or from a non shape memory metal The plaque disrupting formation may be capable of being deformed as the balloon moves from the collapsed condition to the expanded condition. The formation may be welded or otherwise joined to the outer surface of the balloon.

In certain embodiments, the helical centreline of the balloon rotates around a longitudinal axis, and the plaque disrupting formation is arranged so that when the balloon is in the expanded condition it faces radially outwardly with respect to the longitudinal axis. It may sit on the radially outermost point on the balloon cross-section. It is expected that a balloon having a helical centreline (and hence a helical shape) will exert the greatest pressure when expanded where it faces radially outwardly with respect to the longitudinal axis. Hence, by providing the plaque disrupting formation in this region a desired radially outward pressure for plaque disruption can be achieved.

A helix has a pitch and an amplitude. The pitch of the helical centre line may be substantially constant along the length of the balloon. The pitch may vary along the length of the balloon. For example, the pitch in a region adjacent to a longitudinal end of the balloon may be longer than the pitch in a region nearer to the middle of the balloon. The amplitude of the helical centre line may be substantially constant along the length of the balloon. The amplitude may vary along the length of the balloon. For example, the amplitude in a region adjacent to a longitudinal end of the balloon may be smaller than the amplitude in a region nearer to the middle of the balloon.

A helix may be considered as being left-handed or right-handed. The helical centre line of the balloon may be left handed or right handed.

The plaque disrupting formation may be arranged helically on the balloon outer surface. The helical arrangement may have the same handedness as the helical centreline of the balloon, or it may have the opposite handedness to the helical centreline.

The plaque disrupting formation may be arranged helically on the balloon outer surface with substantially the same pitch as the helical centreline of the balloon. It may have the same pitch but the opposite handedness. In certain embodiments, the plaque disrupting formation has substantially the same pitch as the balloon helical centreline, as well as the same handedness. In these arrangements, if the helices are in phase, then the plaque disrupting formation may be arranged so that when the balloon is in the expanded condition it faces radially outwardly with respect to the longitudinal axis about which the helical centreline rotates. The plaque disrupting formation can then exert a relatively high pressure for plaque disruption.

Alternatively, the plaque disrupting formation may have the same pitch and handedness as the helical centreline, but it may be out of phase therewith.

The plaque disrupting formation may extend longitudinally of the balloon. It can therefore disrupt plaque over a given length of a vessel when the balloon is expanded. When the balloon is in the expanded condition, the plaque disrupting formation may extend continuously over a lengthwise portion of the balloon, or it may extend over a lengthwise portion of the balloon as a plurality of plaque disrupting formation portions arranged at longitudinal intervals. For example, a plurality of blades may be arranged at longitudinal intervals.

There may be a single plaque disrupting formation or there may be a plurality of plaque disrupting formations. There may for example be three plaque disrupting formations. This would be a suitable number in the case of a balloon which has a three-wing configuration when in the collapsed condition.

If there is just one plaque disrupting formation, when considering a transverse section of the balloon when in the expanded condition, just the one plaque disrupting formation may be observed on the outer surface of the balloon. The one plaque disrupting formation may be continuous over a lengthwise portion of the balloon, or may be provided as a plurality of plaque disrupting formation portions arranged at longitudinal intervals.

If there is a plurality of plaque disrupting formations, these may be provided at a circumferential interval or at circumferential intervals around the balloon outer surface. When considering a transverse section of the balloon, a plurality of plaque disrupting formations may be observed on the outer surface of the balloon. One or more of the plurality may be continuous over a lengthwise portion of the balloon, or may be provided as a plurality of plaque disrupting formation portions arranged at longitudinal intervals.

Each of the plural plaque disrupting formations may be arranged helically on the balloon outer surface. Each may have the same pitch as the helical centreline of the balloon. Each may have the same handedness as the helical centreline, or each may have the opposite handedness of the helical centreline. One or more formations may have the same handedness as the helical centreline of the balloon, and one or more formations may have the opposite handedness. One of the helical plaque disrupting formations may be in phase with the balloon helical centreline, and one or more of the helical plaque disrupting formations may be out of phase therewith.

The outer surface of the balloon will generally have a notional longitudinally and helically extending line which when the balloon is in the expanded condition faces radially outwardly with respect to the longitudinal axis about which the helical centreline of the balloon rotates. The outer surface may be considered as having a notional substantially helically and longitudinally extending part (or notional helical strip) which has a width in the circumferential direction subtending an angle with respect to the helical centre line and along which said notional line extends along a locus of points each half way across the width. The notional line can be regarded as a centreline of the notional substantially helically and longitudinally extending part. The angle may be 30 or 25 or 20 or 15 or 10 or 5 degrees, for example.

Just one plaque disrupting formation may be provided on this part of the balloon outer surface, or plural plaque disrupting formations may be provided on this part. The or each plaque disrupting formation may be continuous over a lengthwise portion of the balloon, or may be provided as a plurality of plaque disrupting formation portions arranged at longitudinal intervals. Such formations may be closely spaced from each other in the circumferential direction. As this is a part of the outer surface which is expected to exert maximum pressure on the plaque as the balloon expands, it may be desirable to provide more than one plaque disrupting formation along this part. The plural formations may contribute to the plaque disrupting efficiency by engaging with the vessel/plaque surface to ensure effective direction of the formation to the plaque surface thus maximising the force applied.

The balloon may comprise a central shaft. The balloon may thus comprise an expandable wall which in the collapsed condition of the balloon lies close to the shaft and which is expandable radially outwardly from the shaft to cause the balloon to adopt the expanded condition thereof. In such arrangements, the expandable wall provides the balloon outer surface.

In certain embodiments, when the balloon is in the collapsed condition, it is divided into a plurality of pleats which are wrapped around a central shaft. Two or more pleats may be provided. In one possible arrangement, three pleats are provided, but less or more than three may be used. When the balloon is in a pleated state, the plaque disrupting formation may be provided on the balloon outer surface so as to face radially outwardly. This can avoid contact between the plaque disrupting formation, which may for example comprise a sharp cutting blade, and other portions of the balloon outer surface when it is in the collapsed condition. This can avoid damage to the balloon.

The pleats may each have a radially inner fold line, and the radially inner fold line may extend helically around the central shaft. If the fold line extends helically around the central shaft, then the pleats will also tend to follow a helical configuration when wrapped around the shaft. Therefore, the plaque disrupting formation on the balloon outer surface may follow a helical path when the balloon is in the collapsed condition. This is a convenient way of ensuring that the plaque disrupting formation faces radially outwardly when the balloon is in the collapsed condition.

The plaque disrupting formation may be provided adjacent to an exterior edge of a pleat.

The plaque disrupting formation may be provided on the balloon outer surface so as to be covered by at least one of the pleats when the balloon is in the collapsed condition. This arrangement can provide protection to the vessel.

In certain embodiments, the plaque disrupting formation is attached continuously along its length to the balloon outer surface. However, as discussed below, there may be other attachment arrangements for the plaque disrupting formation.

When the helical balloon is collapsed on to a central longitudinal axis, a plaque disrupting formation (single or plural) appended to the balloon outer surface may not be able to follow the pleats as the fold line extends helically around the central shaft. Since the plaque disrupting formation is designed to be on the outer surface of a balloon having, when in the expanded condition, a centre line which follows a substantially helical path, the end to end length of the plaque disrupting formation will be longer than the (cone to cone) length of the collapsed balloon along its longitudinal axis. Physical and mechanical limitations of the materials of the plaque disrupting formation may prevent it from comfortably following the helical path (e.g. around the balloon pleats) when the balloon is in the collapsed condition, potentially resulting in kinking, twisting, or adverse interactions with the balloon. A possible solution is to keep the e.g. longitudinal centre portion of the helical balloon outer surface and the plaque disrupting formation independent of each other (detached).

The plaque disrupting formation may be fixed at one end thereof relative to the balloon outer surface and may not be attached to the outer surface over a lengthwise extending portion of the balloon. In certain embodiments, the plaque disrupting formation is attached at one end thereof to an end portion of the balloon, the end portion belonging for example to the balloon shaft or to the balloon outer surface, and is not attached to the outer surface over a lengthwise extending portion of the balloon.

The plaque disrupting formation may be fixed at both ends thereof relative to the balloon outer surface. The plaque disrupting formation may be attached to respective end portions of the balloon at each end of the formation. The balloon may collapse independently of the plaque disrupting formation (e.g. blade or wire). The plaque disrupting formation, such as a blade or wire, can then be wrapped over the longitudinal shaft of the collapsed balloon. This can avoid damage to the balloon due to pinching or kinking of the plaque disrupting formation. The plaque disrupting formation, such as a cutting or scoring blade or wire, can be configured using a shape memory material such that on expansion of the helical balloon, the plaque disrupting formation will be expanded outwards by the balloon of helical centre line and contact the outer surface of the balloon in any of the desired configurations described herein in order to exert the desired disrupting force on the plaque of the vessel.

In certain embodiments, the plaque disrupting formation is fixed at one end thereof relative to the balloon outer surface, for example being attached at said one end to an end portion of the shaft or of the balloon outer surface such as the balloon neck, and comprises a holder at its other end, the holder being movable relative to the balloon outer surface. For example, the plaque disrupting formation may be fixed relative to the balloon outer surface at a distal end thereof and the holder may be provided at a proximal end. Distal and proximal ends may be considered with respect to a catheter which is used to deliver the balloon to a treatment site.

In certain embodiments, the holder is arranged to be axially movable. It may be axially movable on a shaft of the balloon or a shaft of a delivery catheter. The holder may be arranged to be rotatably movable. It may be rotatably movable on a shaft of the balloon or a shaft of a delivery catheter. The holder may comprise a ring. A ring can be designed to be axially slidable and/or rotatable on a shaft.

A method of ensuring effective plaque disrupting formation and balloon positioning in the collapsed configuration may be to fix the plaque disrupting formation(s) to a longitudinal shaft of the balloon at the distal end only. The plaque disrupting formation(s) at the proximal end may be attached to a circular ring which is free to move over a shaft of e.g. the delivery catheter at the proximal end of the helical balloon. The helical balloon can be collapsed independently of the plaque disrupting formation(s), avoiding damage to the balloon. As the plaque disrupting formation(s) is or are collapsed onto the balloon, the ring can allow the collapsed plaque disrupting formation(s) to take up a pre-set position configuration in one of two ways:

a) The circular ring can rotate around the shaft and allow the plaque disrupting formation(s) to wrap over the helical balloon without being constrained at one end. This will allow plaque disrupting formation(s) which is or are long enough to be orientated in a spiral fashion which matches the substantially helical path in the expanded configuration, to wrap around the collapsed balloon in a manner that reduces the profile and minimises strains on the wire.

b) The circular ring can slide proximally (away from the balloon) along the shaft to allow the relatively long plaque disrupting formation(s) to collapse onto the balloon in a manner that reduces the profile and minimises strains on the wire.

On expansion of the balloon, the ring will allow the plaque disrupting formation(s) to move readily and take a line which follows a substantially helical path along the outer surface of the helical balloon.

Known balloons, once they have been positioned at a treatment site, unwrap from a crimped or collapsed state to an expanded state. As they do so they impart a shearing force on the vessel wall, generally in the circumferential direction along the vessel wall. The shearing forces during inflation have been linked to the creation of vessel dissections.

In certain embodiments of the invention, the balloon may comprise hoop wires extending circumferentially of the balloon when in the expanded condition. The hoop wires may be spaced apart from each other in the lengthwise direction of the balloon. When the balloon is in the collapsed condition, the hoop wires would be folded and collapsed. During expansion, the hoop wires can contact the vessel wall preferentially to the balloon wall and limit the risk of vessel wall damage.

The inner diameter of the hoop wires may be smaller (generally only slightly smaller) than the outer diameter of the inflated balloon. It should be noted that the balloon will normally be made of a material which is relatively inelastic, such that the balloon has an inflated diameter which is predetermined. The use of constraining hoop wires can limit the possibility for the balloon to impart damaging shearing forces on the vessel during expansion and as a result may reduce the likelihood of vessel dissections. In the expanded state the hoop wires may cause the balloon to bulge up slightly between the hoop wires. The balloon would form small pillow shapes between the hoop wires.

The balloon may be provided with at least one lengthwise extending member connecting to at least some of the hoop wires. This can provide a structure holding the hoop wires in place. The plaque disrupting formation may act as such a lengthwise extending member, or there be an additional lengthwise extending member, such as a lengthwise extending wire. A lengthwise extending wire may extend helically around the balloon when in the expanded state, as well as lengthwise of the balloon.

When it is desired to withdraw the balloon from the vessel, the balloon is collapsed and the lengthwise extending member may be used to pull the hoop wires out of the vessel.

In certain embodiments, a plurality of lengthwise extending members are provided, which may be circumferentially spaced around the balloon.

The hoop wires may be manufactured from a flexible material with good elastic properties, for example the superelastic alloy nitinol or a similar material.

Viewed from a second aspect, the invention provides an expandable balloon for insertion in a vessel of the human or animal body, the balloon being movable between a collapsed condition and an expanded condition, the balloon having, when in the expanded condition, a centre line which follows a substantially helical path, and the balloon comprising hoop wires extending circumferentially of the balloon when in the expanded condition, the hoop wires being spaced apart from each other in the lengthwise direction of the balloon.

Such a balloon may be used for example in percutaneous transluminal angioplasty (PTA) and so may not have a plaque disrupting formation as described herein. A vessel may be expanded to a helical shape corresponding to the shape of the balloon. The balloon may be used to expand a stent to a helical shape corresponding to the shape of the balloon. The stent may be biased to adopt substantially the same helical shape as the balloon, for example by being made of a shape memory material, or it may be plastically deformed by the balloon to adopt the helical shape thereof.

In other embodiments, the balloon may have such a plaque disrupting formation, so as then to be usable as a cutting or scoring balloon. It may have any of the various optional features described above in relation to the balloon with the plaque disrupting formation.

Considering the balloon of the second aspect, when the balloon is in the collapsed condition, the hoop wires would be folded and collapsed. During expansion, the hoop wires can contact the vessel wall preferentially to the balloon wall and limit the risk of vessel wall damage.

The inner diameter of the hoop wires may be smaller (generally only slightly smaller) than the outer diameter of the inflated balloon. It should be noted that the balloon will normally be made of a material which is relatively inelastic, such that the balloon has an inflated diameter which is predetermined. The use of constraining hoop wires can limit the possibility for the balloon to impart damaging shearing forces on the vessel during expansion and as a result may reduce the likelihood of vessel dissections. In the expanded state the hoop wires may cause the balloon to bulge up slightly between the hoop wires. The balloon would form small pillow shapes between the hoop wires.

The balloon of the second aspect may be provided with at least one lengthwise extending member connecting to at least some of the hoop wires. This can provide a structure holding the hoop wires in place. The inner diameter of the lengthwise extending member may be smaller (generally only slightly smaller) than the outer diameter of the inflated balloon. In the case of embodiments forming pillow shapes where the balloon bulges up, the pillow shapes will have a modified shape, as the balloon will be constrained by both the hoop wires and the lengthwise extending member.

The lengthwise extending member of the balloon of the second aspect may be a lengthwise extending wire. A lengthwise extending wire may extend helically around the balloon when in the expanded state, as well as lengthwise of the balloon.

When it is desired to withdraw the balloon from the vessel, the balloon is collapsed and the lengthwise extending member may be used to pull the hoop wires out of the vessel.

In certain embodiments, a plurality of lengthwise extending members are provided, which may be circumferentially spaced around the balloon.

The hoop wires may be manufactured from a flexible material with good elastic properties, for example the superelastic alloy nitinol or a similar material.

The invention also extends to methods of using the expandable balloon of the first aspect or the second aspect.

Viewed from another aspect, related to the first aspect, the invention provides a method of treating a plaque in a vessel of the human or animal body, the method comprising deploying a balloon in a collapsed condition to a treatment site and expanding the balloon, the balloon comprising a plaque disrupting formation on an outer surface thereof, so that when the balloon is in the expanded condition the plaque disrupting formation exerts pressure on the plaque, and the balloon having, when in the expanded condition, a centreline which follows a substantially helical path.

The balloon used in the treatment method may have the various optional features described herein.

The plaque disrupting formation on the outer surface of the balloon may extend generally helically to follow the shape of the plaque. One method may therefore comprise determining the shape of a plaque, and using a balloon with a plaque disrupting formation extending helically generally to follow the shape of the plaque. The shape of the plaque may be determined by suitable scanning techniques.

BRIEF DESCRIPTION OF THE DRAWINGS

Certain preferred embodiments of the invention will now be described by way of example and with reference to the accompanying drawings, in which.

DETAILED DESCRIPTION

Figure 1:
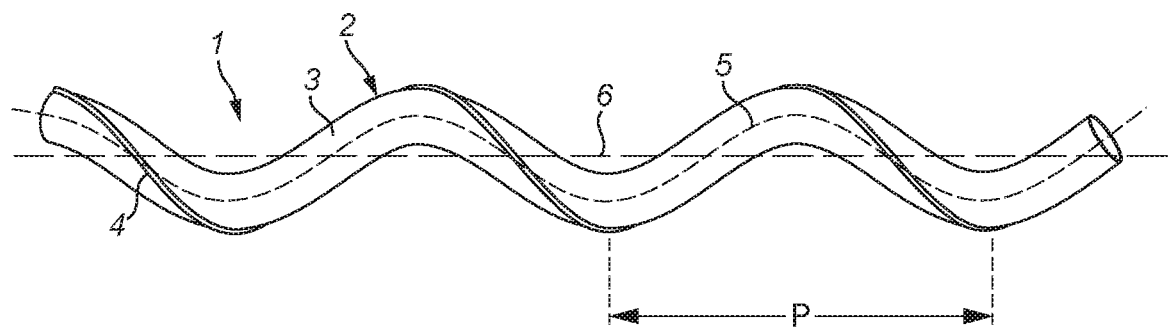
FIG. 1 shows a perspective view of a first embodiment of an expandable balloon.

FIG. 1 shows an expandable balloon 1 having a wall 2 with an outer surface 3. A plaque disrupting formation 4 is provided on the outer surface 3. The formation may be a cutting or scoring blade or it may be a wire, e.g. made of a shape memory alloy such as nitinol.

The balloon 1 has a helical axis 5 which rotates helically about a longitudinal axis 6. The balloon is shown in an expanded condition ex vivo. When the balloon is expanded in vivo it may not adopt the exact shape shown, as it will be constrained by the vessel and any plaque which is intended to be disrupted by the balloon.

The helical centreline 5 of the balloon has a pitch P. In this embodiment the plaque disrupting formation 4 has the same pitch P. The plaque disrupting formation 4 is arranged so that it faces radially outwardly with respect to the longitudinal axis 6. This means that it is likely to be on the part of the balloon which exerts greatest pressure on the vessel and any plaque as the balloon is expanded.

Figure 2:
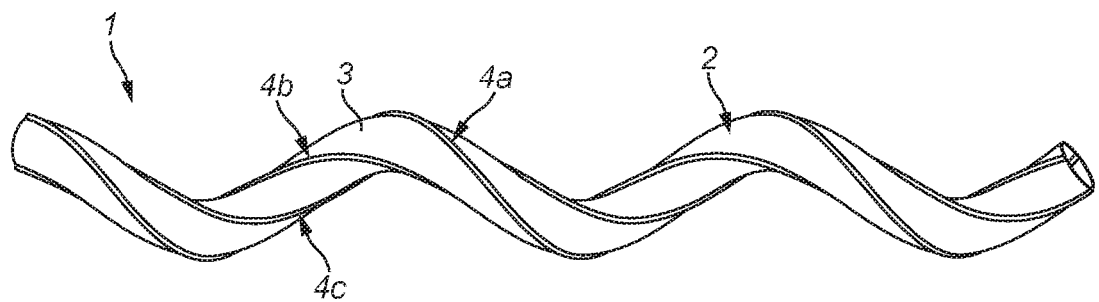
FIG. 2 shows a perspective view of a second embodiment of an expandable balloon.

The balloon 1 shown in FIG. 2 is similar to that of FIG. 1, except that it has three plaque disrupting formations 4*a*, 4*b* and 4*c*. These are provided on the outer surface of the balloon at equal circumferential spacings from each other. Each formation 4*a*, 4*b*, 4*c* has the same helical pitch P as the helical centreline 5 of the balloon. Plaque disrupting formation 4*a* is arranged to face radially outwardly with respect to the longitudinal axis 6.

Figure 3:
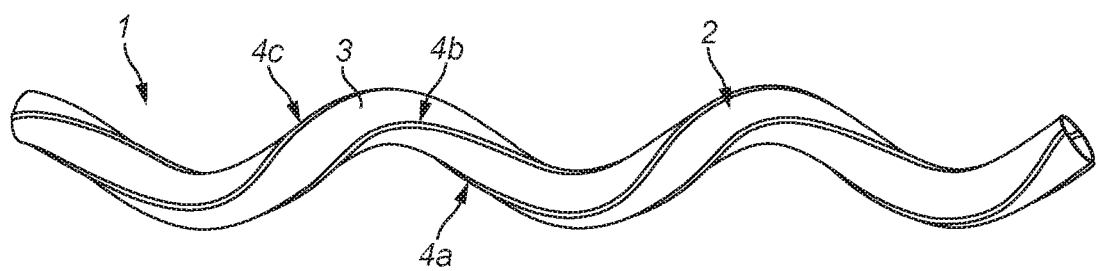
FIG. 3 shows perspective view of a third embodiment of an expandable balloon.

The balloon 1 shown in FIG. 3 has an outer wall 2 with an outer surface 3. On the outer surface 3 plaque disrupting formations 4*a*, 4*b* and 4*c* are provided. The helical centreline 5 of the balloon is a right-handed helix, whereas the plaque disrupting formations 4*a*-4*c* are provided on the balloon outer surface 3 in a left-handed helical configuration.

Figure 4:
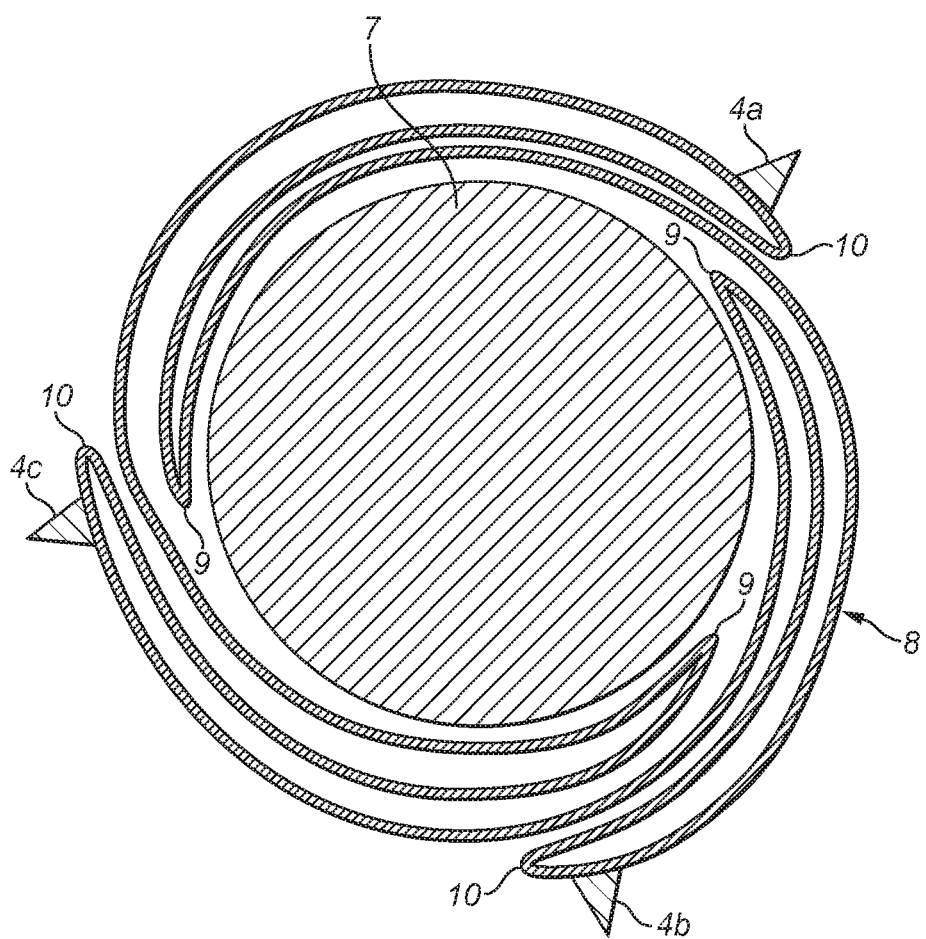
FIG. 4 shows a cross-sectional view of the second embodiment when the balloon is in the collapsed condition.

FIG. 4 shows a cross-sectional view of the balloon of FIG. 2 when in a collapsed condition. The balloon is collapsed onto a central shaft 7. It is formed into three pleats 8 each of which has a radially inner fold line 9. The fold lines 9 extend helically around the central shaft 7. They thus extend along the shaft and around it. Each of the plaque disrupting formations 4*a*-4*c* is provided adjacent to a tip 10 of each pleat 8. The formations 4*a*-4*c* face radially outwardly with respect to the central shaft 7. This arrangement ensures that the plaque disrupting formations 4*a*-4*c* do not engage the wall of the balloon other than where they are attached thereto. Therefore damage to the balloon surface in the collapsed condition can be avoided.

During deployment, the collapsed balloon shown in FIG. 4 may be contained in a sleeve until the balloon is located at the deployment site. The sleeve is then withdrawn and the balloon may be expanded. The plaque disrupting formation or formations then engage the plaque and cut or score or otherwise weaken it. In the case that the plaque disrupting formation faces radially outwardly with respect to the longitudinal axis 5, the required force to rupture the plaque may be achieved with lower balloon inflation pressure and this may be beneficial in limiting collateral damage to the vessel within which the treatment is being conducted.

Figure 5:
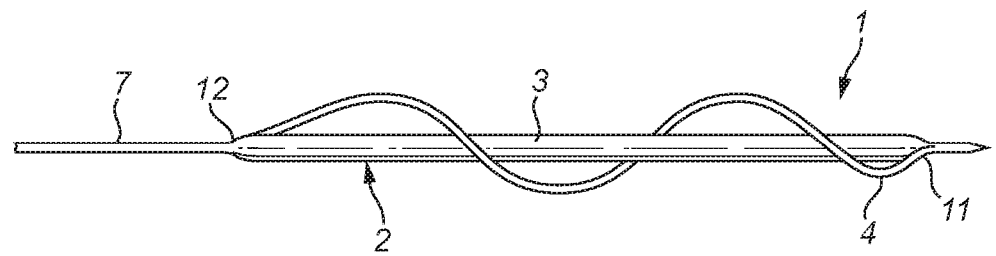
FIG. 5 shows a fourth embodiment of an expandable balloon.

FIG. 5 shows a plaque disrupting formation comprising a wire 4 which is fixed at a distal end 11 to the balloon outer surface 3 and is fixed at a proximal end 12 to the balloon outer surface 3. The balloon 1 is supported on a shaft 7. The balloon 1 is shown in the collapsed condition and the wire 4 is shown as it would be when the balloon is expanded. During delivery on the end of a catheter both the balloon wall 2 and the wire 4 could be constrained inside a sleeve (not shown).

Figure 6:
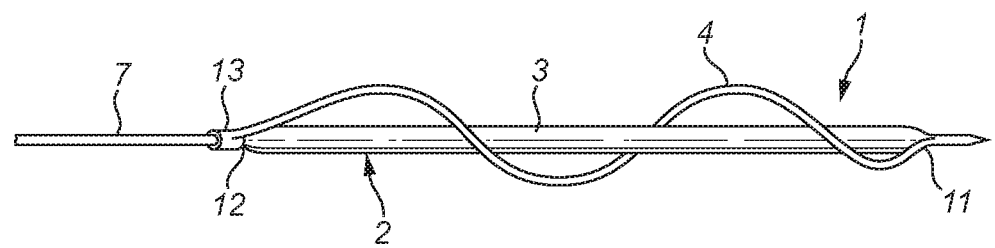
FIG. 6 shows a fifth embodiment of an expandable balloon.

FIG. 6 shows a plaque disrupting formation comprising a wire 4 which is fixed at a distal end 11 to the balloon outer surface 3 and is provided at a proximal end 12 with a ring 13 which is free to move on the shaft 7. The balloon 1 is shown in the collapsed condition and the wire 4 is shown as it would be when the balloon is expanded. During delivery on the end of a catheter both the balloon wall 2 and the wire 4 could be constrained inside a sleeve (not shown).

Figure 7:
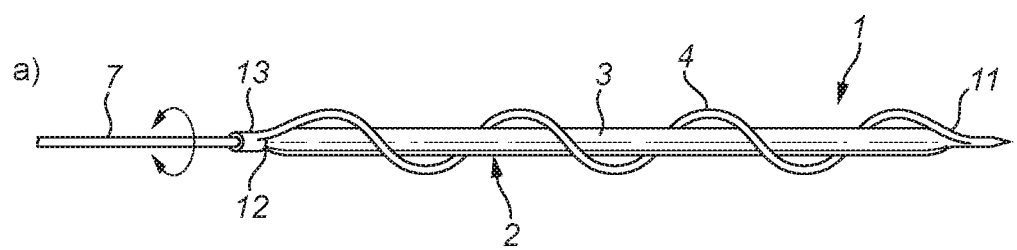
FIG. 7 shows two manners of operation of the fifth embodiment.
Figure 7:
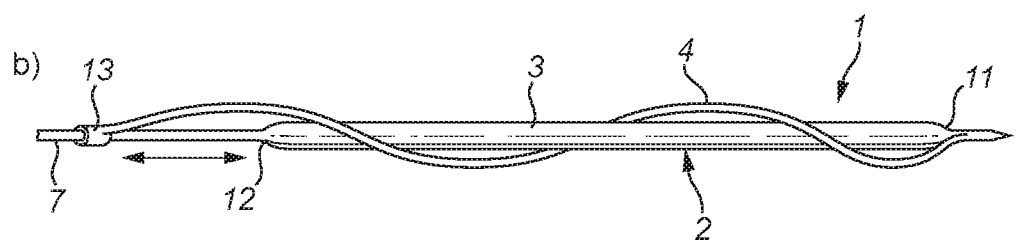

FIG. 7a shows a first manner of operation of a balloon as seen in FIG. 6. The balloon of FIG. 6 is shown in the collapsed condition. Compared to the configuration of FIG. 6, the ring 13 is rotated relative to the fixed distal end 11 of the wire 4, so as to wrap or wind the wire 4 over the collapsed balloon. This reduces the transverse profile of the balloon.

FIG. 7b shows a second manner of operation of a balloon as seen in FIG. 6. The balloon of FIG. 6 is shown in the collapsed condition. Compared to the configuration of FIG. 6, the ring 13 is positioned further from the fixed distal end 11 of the wire 4, so as to wrap or wind the wire 4 over the collapsed balloon. This is achieved by the ring having slid proximally along the shaft 7, away from the distal end 11. This reduces the transverse profile of the plaque disrupting formation and the balloon.

Figure 8:
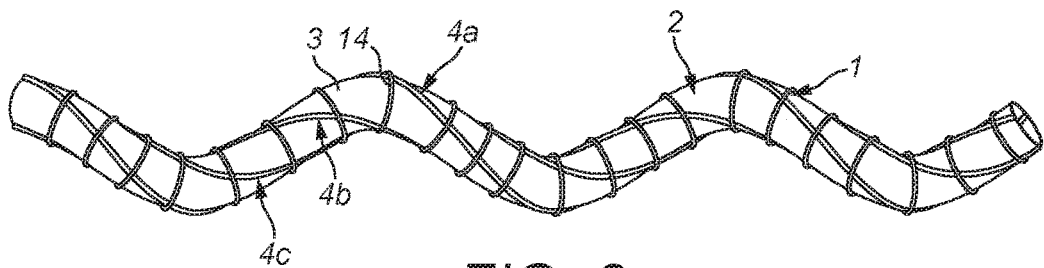
FIG. 8 shows a perspective view of a sixth embodiment of an expandable balloon.

The balloon 1 shown in FIG. 8 is similar to that of FIG. 2, with three plaque disrupting formations 4a, 4b and 4c. These are provided on the outer surface of the balloon at equal circumferential spacings from each other. Each formation 4a, 4b, 4c has the same helical pitch P as the helical centreline 5 of the balloon. Plaque disrupting formation 4a is arranged to face radially outwardly with respect to the longitudinal axis 6.

The balloon of FIG. 8 additionally has hoop wires 14 extending circumferentially of the balloon when in the expanded condition. The hoop wires 14 are spaced apart from each other in the lengthwise direction of the balloon. When the balloon is in the collapsed condition, the hoop wires 14 would be folded and collapsed. During expansion, the hoop wires 14 can contact the vessel wall preferentially to the balloon wall and limit the risk of vessel wall damage.

Figure 9:
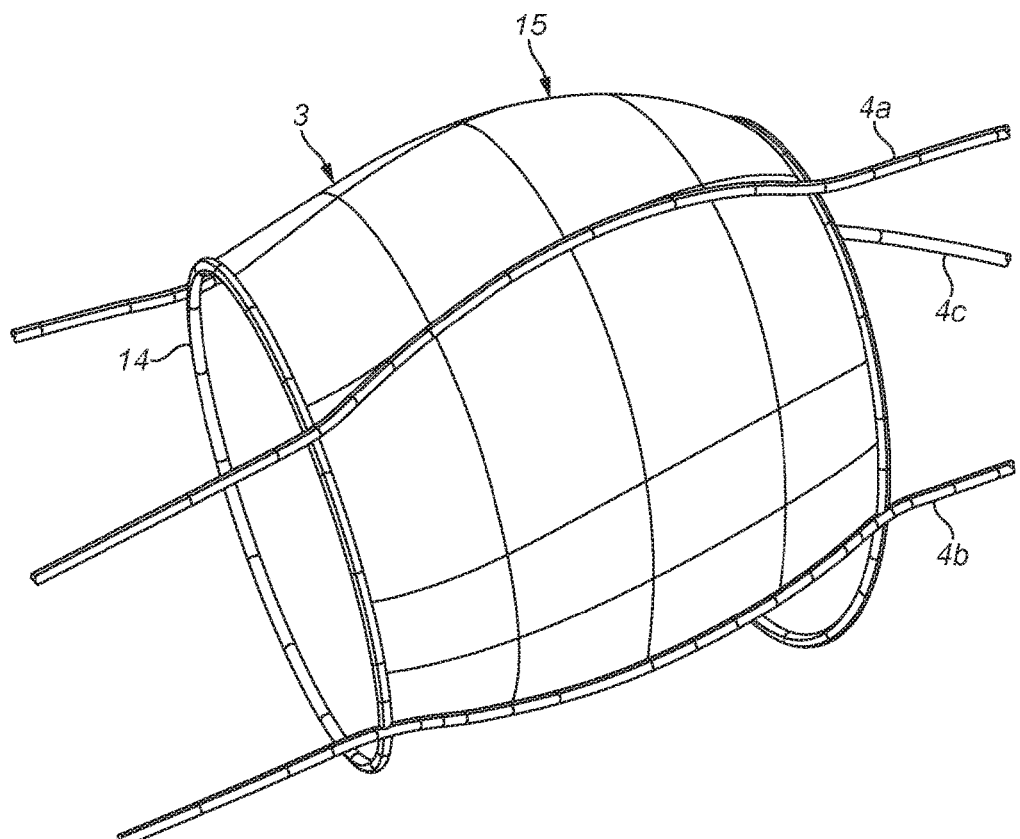
FIG. 9 shows a detail of FIG. 8, to an enlarged scale.

As can be seen in FIG. 9, which shows a detail of the balloon of FIG. 8 to an enlarged scale, the inner diameter of the hoop wires 14 is smaller than the outer diameter of the inflated balloon, i.e. the outer diameter it would have when inflated without being constrained by the hoop wires. It should be noted that the balloon will normally be made of a material which is relatively inelastic, such that the balloon has an unconstrained inflated diameter which is predetermined. The use of constraining hoop wires can limit the possibility for the balloon to impart damaging shearing forces on the vessel during expansion and as a result may reduce the likelihood of vessel dissections.

In the expanded state the hoop wires cause the balloon to bulge up slightly between the hoop wires 14. The balloon forms pillow shapes 15 between the hoop wires. These are present but not shown in FIG. 8, and can be seen in the enlarged view of FIG. 9. The plaque disrupting formations, in the form of helical wires as seen in FIGS. 8 and 9, sit on the balloon outer surface 3 and so in use make contact with the vessel wall.

The balloon of FIGS. 8 and 9 is an exemplary embodiment of both the first and second aspects of the invention.

Figure 10:
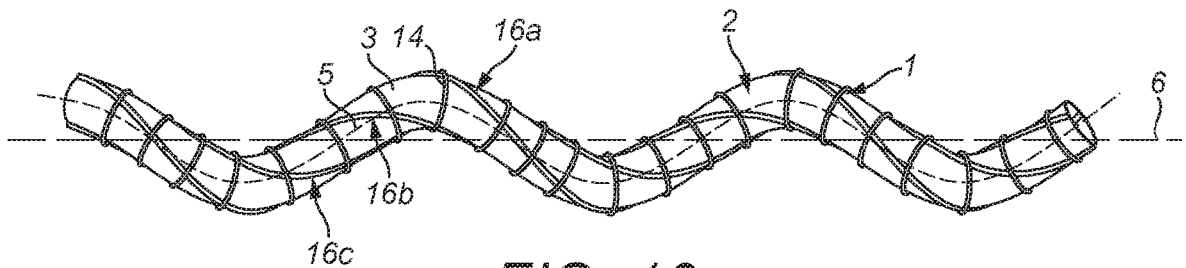
FIG. 10 shows a perspective view of a seventh embodiment of an expandable balloon.
Figure 11:
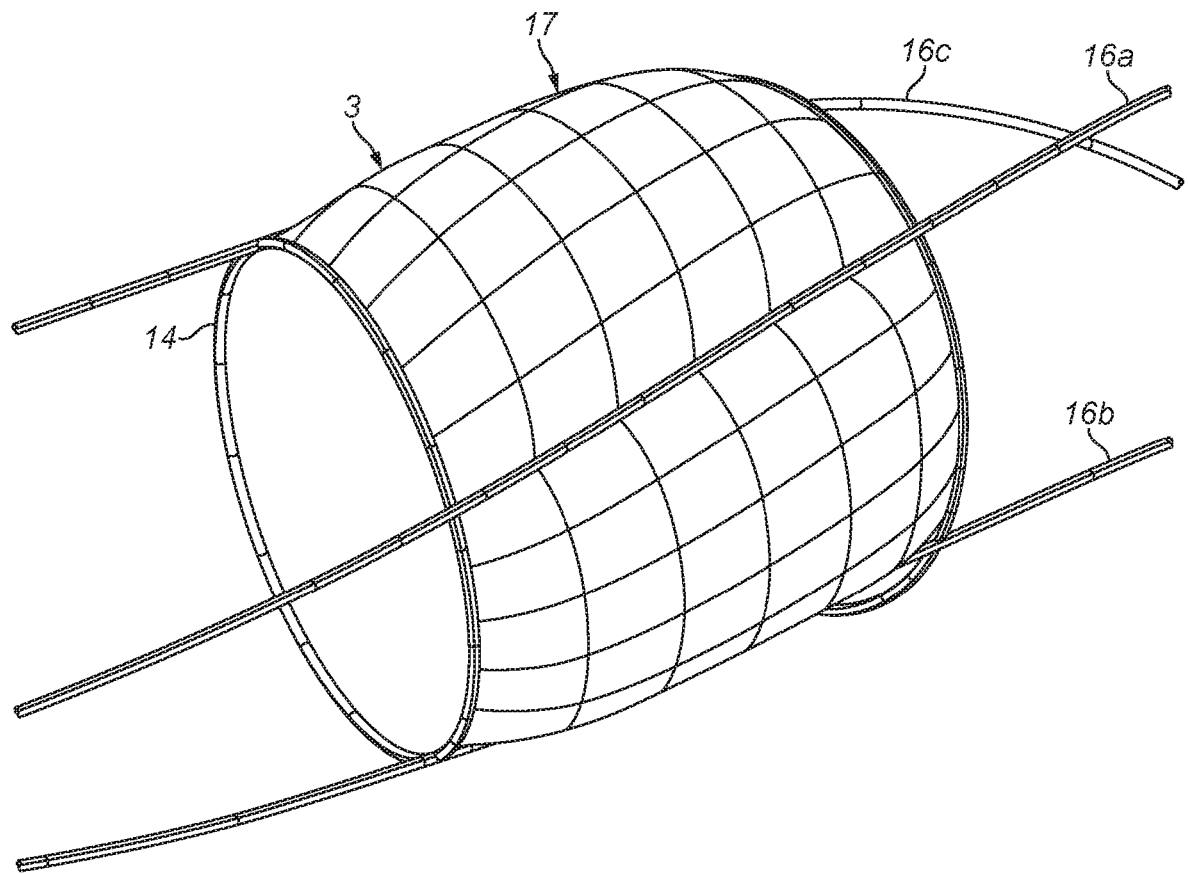
FIG. 11 shows a detail of FIG. 10, to an enlarged scale.

The balloon of FIGS. 10 and 11 is an exemplary embodiment of the second aspect of the invention. These show an expandable balloon 1 for insertion in a vessel of the human or animal body, the balloon being movable between a collapsed condition and an expanded condition, the balloon having, when in the expanded condition, a helical axis 5 which rotates helically about a longitudinal axis 6, and the balloon comprising hoop wires 14 extending circumferentially of the balloon when in the expanded condition, the hoop wires 14 being spaced apart from each other in the lengthwise direction of the balloon.

When the balloon is in the collapsed condition, the hoop wires 14 would be folded and collapsed. During expansion, the hoop wires 14 can contact the vessel wall preferentially to the balloon wall and limit the risk of vessel wall damage.

As can be seen in FIG. 11, which shows a detail of the balloon of FIG. 10 to an enlarged scale, the inner diameter of the hoop wires 14 is smaller than the outer diameter of the inflated balloon, i.e. the outer diameter it would have when inflated without being constrained by the hoop wires. It should be noted that the balloon will normally be made of a material which is relatively inelastic, such that the balloon has an unconstrained inflated diameter which is predetermined. The use of constraining hoop wires can limit the possibility for the balloon to impart damaging shearing forces on the vessel during expansion and as a result may reduce the likelihood of vessel dissections.

The balloon of FIGS. 10 and 11 has lengthwise extending members in the form of helical wires 16a, 16b and 16c, which are connected to the hoop wires 14. The helical wires are circumferentially spaced around the balloon. The inner diameter of the helical wires is smaller than the outer diameter of the inflated balloon. Pillow shapes 17 are formed where the balloon bulges up between the constraints of both the hoop wires 14 and the helical wires 16a, 16b and 16c. The pillow shapes are present but not shown in FIG. 10, and can be seen in the enlarged view of FIG. 11. In use, once the balloon is fully expanded, the helical wires 16a, 16b and 16c do not make contact with the vessel wall.

When it is desired to withdraw the balloon from the vessel, the balloon is collapsed and the helical wires 16a, 16b and 16c may be used to pull the hoop wires out of the vessel.

The balloon of FIGS. 10 and 11 may be used for example in percutaneous transluminal angioplasty (PTA) and does not have plaque disrupting formations. A vessel may be expanded to a helical shape corresponding to the shape of the balloon. The balloon may be used to expand a stent to a helical shape corresponding to the shape of the balloon. The stent may be biased to adopt substantially the same helical shape as the balloon, for example by being made of a shape memory material, or it may be plastically deformed by the balloon to adopt the helical shape thereof.

In some instances a plaque may have a generally helical pattern in the vessel. An optimal plaque disrupting balloon design can take account of the helical nature of the plaque. For example, it may follow the morphology of the plaque, or it may be arranged with opposite handedness to the helical morphology of the plaque so as to tend to cut across it.

The invention claimed is:

1. An expandable balloon for insertion in a vessel of the human or animal body, the balloon being movable between a collapsed condition and an expanded condition to expand the vessel, wherein a plaque disrupting member is disposed on an outer surface of the balloon when in the expanded condition, the plaque disrupting member extending over a lengthwise portion of the balloon, and the balloon having, when in the expanded condition, a centre line which follows a substantially helical path, wherein the plaque disrupting member is arranged helically on the balloon outer surface with substantially the same pitch as a helical centre line of the balloon, and wherein the plaque disrupting member is fixed at one end thereof relative to the balloon outer surface and is not attached to the balloon outer surface over a lengthwise extending portion of the balloon and, wherein the plaque disrupting member comprises a holder at its other end which is movable relative to the balloon outer surface.

2. A balloon as claimed in claim 1, wherein the helical centre line rotates around a longitudinal axis, and the plaque disrupting member is arranged so that when the balloon is in the expanded condition it faces radially outwardly with respect to the longitudinal axis.

3. A balloon as claimed in claim 1, wherein the helical arrangement of the plaque disrupting member has the same handedness as the helical centre line of the balloon.

4. A balloon as claimed in claim 1, wherein the helical arrangement of the plaque disrupting member has the opposite handedness to the helical centre line of the balloon.

5. A balloon as claimed in claim 1, comprising a plurality of plaque disrupting members provided at a circumferential interval or at circumferential intervals around the balloon outer surface.

6. A balloon as claimed in claim 1, wherein when the balloon is in the collapsed condition, it is divided into a plurality of pleats which are wrapped around a central shaft.

7. A balloon as claimed in claim 6, wherein the pleats each have a radially inner fold line, and wherein the radially inner fold line extends helically around the central shaft.

8. A balloon as claimed in claim 6, wherein the plaque disrupting member is provided on the balloon outer surface so as to face radially outwardly when the balloon is in the collapsed condition.

9. A balloon as claimed in claim 6, wherein the plaque disrupting member is provided on the balloon outer surface so as to be covered by at least one of the pleats when the balloon is in the collapsed condition.

10. A balloon as claimed in claim 1, wherein the holder is arranged to be axially movable.

11. A balloon as claimed in claim 1, wherein the holder is arranged to be rotatably movable.

12. A balloon as claimed in claim 1, wherein the holder comprises a ring.

13. A balloon as claimed in claim 1, wherein the plaque disrupting member extends continuously over a lengthwise portion of the balloon.

14. A balloon as claimed in claim 1, wherein the plaque disrupting member extends over a lengthwise portion of the balloon as a plurality of plaque disrupting members arranged at longitudinal intervals.

15. A balloon as claimed in claim 1, wherein the plaque disrupting member comprises a cutting blade or wire.

16. A balloon as claimed in claim 1, wherein the balloon has, when in the expanded condition, the helical centre line which follows a substantially helical path so that the balloon has a helical shape, and the balloon is configured so that when the balloon is expanded in the vessel the balloon expands the vessel to a helical shape corresponding to the helical shape of the expanded balloon as constrained by the vessel.

17. A method of treating a plaque in a vessel of the human or animal body, the method comprising deploying a balloon in a collapsed condition to a treatment site and expanding the balloon to expand the vessel, wherein a plaque disrupting member is disposed on an outer surface of the balloon, the plaque disrupting member extending over a lengthwise portion of the balloon, so that when the balloon is in the expanded condition the plaque disrupting member exerts pressure on the plaque, and the balloon having, when in the expanded condition, a centre line which follows a substantially helical path, wherein the plaque disrupting member is arranged helically on the balloon outer surface with substantially the same pitch as a helical centre line of the balloon, and wherein the plaque disrupting member is fixed at one end thereof relative to the balloon outer surface and is not attached to the balloon outer surface over a lengthwise extending portion of the balloon and, wherein the plaque disrupting member comprises a holder at its other end which is movable relative to the balloon outer surface.

18. A method as claimed in claim 17, comprising determining the shape of a plaque, and using a balloon with a plaque disrupting member extending helically generally to follow the shape of the plaque.

19. The method as claimed in claim 17, wherein the plaque disrupting member comprises a cutting blade or wire.

20. The method as claimed in claim 17, wherein the balloon has, when in the expanded condition, a helical shape, and the balloon is configured so that when the balloon is expanded in the vessel the balloon expands the vessel to a helical shape corresponding to the helical shape of the expanded balloon as constrained by the vessel.

* * * * *